United States Patent [19]

Fuchs

[11] 4,035,379

[45] July 12, 1977

[54] PROCESS FOR THE PRODUCTION OF 2-AMINO-BENZOTHIAZOLES

[75] Inventor: Rudolf Fuchs, Lausanne, Switzerland

[73] Assignee: Lonza Ltd., Gampel, Valais, Switzerland

[21] Appl. No.: 651,299

[22] Filed: Jan. 22, 1976

[30] Foreign Application Priority Data

Jan. 22, 1975 Switzerland .......................... 758/75

[51] Int. Cl.² ...................................... C07D 277/82
[52] U.S. Cl. .............................................. 260/305
[58] Field of Search .................................. 260/305

*Primary Examiner*—R. J. Gallagher
*Attorney, Agent, or Firm*—Fisher, Christen & Sabol

[57] ABSTRACT

A process for the production of a 2-amino-benzothiazole having the formula:

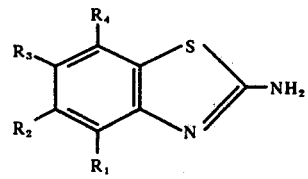

wherein $R_1$, $R_2$, $R_3$ and $R_4$ are the same or different and are hydrogen, halogen, alkyl or alkoxy. A phenylthiourea having the formula:

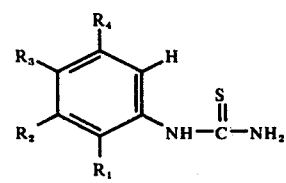

wherein $R_1$, $R_2$, $R_3$ and $R_4$ are defined as above, is added to a cyclization agent in the absence of a solvent and allowing the phenylthiourea to cyclize to form 2-amino-benzothiazole in salt form. Filtering the salt of the 2-amino-benzothiazole out of the reaction mixture.

14 Claims, No Drawings

PROCESS FOR THE PRODUCTION OF 2-AMINO-BENZOTHIAZOLES

BACKGROUND OF THIS INVENTION

1. Field of This Invention

This invention relates to a process for the production of certain 2-amino-benzothiazoles.

2. Prior Art

German published application no. 1,916,599 discloses producing 2-amino-6-methoxy-benzothiazole by reaction of a halogen or sulfur halide as a cyclization agent with p-methoxy phenylthiourea in the presence of an inert solvent. The process is characterized in that a pH value of 2.6 to 3.4 is obtained in an aqueous solution of the salt of the 2-amino-6-methoxy-benzothiazole at a temperature between 40° and 85° C. and in that the precipitated impurities are separated.

4- and 6-substituted 2-amino-benzothiazoles are produced by cyclization of 2- and 4-substituted N-arylthiourea using bromine, sulfurylchloride, chlorine, $SCl_2$ or $SbCl_5$ in chloroform, chlorobenzene, ethylene, dichloride or nitrobenzene. (See *J. Chem. Soc.* (C), 1969, p. 268.)

The known processes have the disadvantages of requiring relatively large quantities of solvent, from which the end product must again be separated after the reaction is completed. The reaction time, moreover, is very long in the case of the known processes.

BROAD DESCRIPTION OF THIS INVENTION

An object of this invention is to provide a process for the production of certain 2-amino-benzothiazoles which has a short reaction time and produces a pure product in a good yield. Another object of this invention is to provide a process that has a reaction step that is conducted in the absence of a solvent. Other objects and advantages of this invention are set out herein or are obvious herefrom to one ordinarily skilled in the art.

The process of this invention achieves the objects and advantages of this invention.

This invention involves a process for the production of a 2-amino-benzothiazole having the formula:

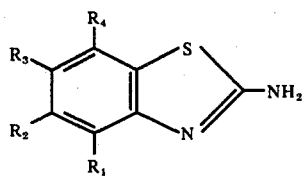

wherein $R_1$, $R_2$, $R_3$ and $R_4$ are the same or different and are hydrogen, halogen alkyl or alkoxy. The process includes adding a phenylthiourea having the formula:

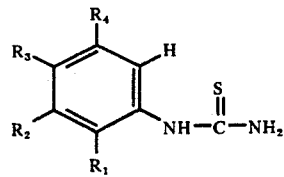

wherein $R_1$, $R_2$, $R_3$ and $R_4$ are defined as above, to a cyclization agent in the absence of a solvent and allowing the phenylthiourea to cyclize to form the 2-amino-benzothiazole in salt form. The salt of the 2-amino-benzothiazole is filtered out of the reaction (cyclization) mixture.

Effectively the cyclization is conducted for between 1 and 10 hours, and at a temperature between 30° and 100° C. Preferably the cyclization agent is a sulfur halide, and most preferably is disulfur dichloride. Effectively the cyclization agent is present in an amount which is at least 6 times its stoichiometric amount (in relation to the phenylthiourea), and preferably is present in an amount which is between 10 and 12 times its stoichiometric amount.

The salt of the 2-amino-benzothiazole, after the filtration step, is purified and placed in the free or base compound form. Typically the salt of the 2-amino-benzothiazole, after the filtration step, is washed with a solvent for the cyclization agent to remove any cyclization agent from the 2-amino-benzothiazole. The 2-amino-benzothiazole is then dissolved in water. The solution is neutralized with a basic agent, the 2-amino-benzothiazole precipitating in crystalline form. The 2-amino-benzothiazole precipitated is removed from the neutralized solution. Such removal is preferably achieved by filtration or centrifugation. Between the dissolution step and the neutralization step, the solution containing the salt of the 2-amino-benzothiazole can be treated with activated charcoal to bleach and clarify such solution. Preferably the basic agent is sodium or potassium carbonate or hydroxide in aqueous solution. Most preferably the basic agent is an aqueous ammonia solution.

DETAILED DESCRIPTION OF THIS INVENTION $R_1$, $R_2$, $R_3$ and $R_4$ can be a halogen, such as, chlorine, bromine, iodine and fluorine.

$R_1$, $R_2$, $R_3$ and $R_4$ can be an alkyl group having one to ten carbon atoms and preferably an alkyl group having one to four carbon atoms. Examples of alkyls which $R_1$, $R_2$, $R_3$ and $R_4$ can be are methyl, ethyl, propyl, isopropyl, butyl, isobutyl, tert.-butyl, 2-butyl, amyl, 2-methyl-1-butyl, isoamyl, neopentyl, 2-pentyl, tert.-amyl, 3-pentyl, 3-methyl-2-butyl, hexyl, 2-methyl-1-pentyl, isohexyl, 3-methyl-1-pentyl, 2-ethyl-1-butyl, 3-methyl-2-pentyl, 2,3-dimethyl-pentyl, 4-methyl-2-pentyl, 2-hexyl, 2-methyl-3-pentyl, 3-hexyl, 2,3-dimethyl-3-butyl, 2-methyl-2-pentyl, 2,3-dimethyl-2-butyl, 3-methyl-3-pentyl, 2,4-dimethyl-3-pentyl, heptyl, 2,4-dimethyl-1-pentyl, 2,3,3-trimethyl-2-butyl, octyl, 2-octyl, 2,4,4-trimethyl-1-pentyl, nonyl, 2,3,4-trimethyl-1-pentyl, decyl, 2,3,4-trimethyl-2-pentyl and 3,3,4-trimethyl-1-pentyl.

$R_1$, $R_2$, $R_3$, and $R_4$ can be an alkoxy group having one to ten carbon atoms and preferably an alkoxy group having one to four carbon atoms. Examples of alkyls which $R_1$, $R_2$, $R_3$ and $R_4$ can be are methoxy, ethoxy, propoxy, isopropoxy, butoxy, isobutoxy, tert.-butoxy, 2-butoxy, amoxy, 2-methyl-1-butoxy, isoamoxy, neopentoxy, 2-pentoxy, tert.-amoxy, 3-penoxy, 3-methyl-2-butoxy, hexoxy, 2-methyl-1-pentoxy, isohexoxy, 3-methyl-1-pentoxy, 2-ethyl-1-butoxy, 3-methyl-2-pentoxy, 2,3-dimethyl-pentoxy, 4-methyl-2-pentoxy, 2-hexoxy, 2-methyl-3-pentoxy, 3-hexoxy, 2,3-dimethyl-3-butoxy, 2-methyl-2-pentoxy, 2,3-dimethyl-2-butoxy, 3-methyl-3-pentoxy, 2,4-dimethoxy-3-pentoxy, heptoxy, 2,4-dimethyl-1-pentoxy, 2,3,3-trimethyl-2-butoxy, octoxy, 2-octoxy, 2,4,4-trimethyl-1-pentoxy, nonoxy, 2,3,4-trimethyl-1-pentoxy, decoxy, 2,3,4-trimethyl-2-pentoxy, and 3,3,4-trimethyl-1-pentoxy.

The preferred cyclization (or cyclizing) agent is disulfur dichloride ($S_2Cl_2$). (Disulfur dichloride is also termed sulfur monochloride or sulfur subchloride and its formula is also given as SCl.) But any phenylthiourea cyclization agent can be used. Examples of other useful (phenylthiourea) cyclization agents are the halogens, such as, bromine, chlorine, flourine and iodine, the sulfur halides, such as, sulfur monochloride, ($S_2Br_2$), sulfur dichloride ($SCl_2$), sulfur tetrachloride ($SCl_4$), sulfur monofluoride ($S_2F_2$), sulfur tetrafluoride ($SF_4$), disulfur decafluoride ($S_2F_{10}$) and sulfur hexafluoride ($SF_6$), the sulfoxy halides, such as, sulfuryl chloride ($SO_2Cl_2$), pyrosulfuryl chloride ($S_2O_5Cl_2$), sulfuryl fluoride ($SO_2F_2$), sulfuryl chloride fluoride ($SO_2ClF$), thionyl bromide ($SOBr_2$), thionyl chloride ($SOCl_2$), thionyl fluoride ($SOF_2$), thionyl chloride fluoride ($SOClF$), $S_2OCl_4$ and $S_2O_3Cl_4$, $SbI_5$, $SbF_5$ and $SbCl_5$.

The cyclization is used effectively in an amount which is at least 6 times its stoichiometric amount and preferably in an amount which is 10 to 12 times its stoichiometric amount. A stoichiometric surplus greater than 12 times of the cyclization agent has no influence on the course and result of the reaction.

The cyclization agent, recovered after filtration out of the chlorobhydrate of the 2-amino-benzothiazole from the cyclization mixture can be reused several times without any problems or troubles.

The reaction temperatures for the cyclization is effectively between 30° to 100° C. Preferably the reaction (cyclization) is carried out between 50° to 60° C. The reaction can be carried out at atmospheric pressure or at higher or lower pressures. The cyclization is effectively conducted over a time period of 1 to 10 hours.

After cyclization (reaction), the salt of the 2-amino-benzothiazole is filtered out of the reaction solution. Then the cyclization agent residue can be washed out of the salt of the 2-amino-benzothiazole. An organic inert solvent, in which the cyclization agent is soluble, for example, ethylene dichloride, pentane, etc. is effectively used as the washing fluid.

The salt of the 2-amino-benzothiazole then can be dissolved in water and, if desired, treated with activated charcoal for bleaching and clarification.

The solution can be neutralized with a basic agent (base), whereby the 2-amino-benzothiazole derivative is obtained in crystalline form. Any suitable base can be used. Examples of useful alkali metal and alkaline earth metal carbonate basic agents are sodium carbonate, potassium carbonate, magnesium carbonate, cesium carbonate, barium carbonate, radium carbonate, calcium carbonate, strontium carbonate, beryllium carbonate, rubidium carbonate and lithium carbonate, another useful carbonate is ammonium carbonate. Examples of useful alkali metal and alkaline earth hydroxide basic agents are sodium hydroxide, potassium hydroxide, magnesium hydroxide, calcium hydroxide, barium hydroxide, strontium hydroxide, beryllium hydroxide, cesium hydroxide and lithium hydroxide. Another useful hydroxide is ammonium hydroxide. Examples of useful alkali metal or alkaline earth metal alcoholates or alkoxides basic agents are sodium methoxide, sodium ethoxide and magnesium methoxide. Examples of useful alkali metal or alkaline earth metal oxide basic agents are sodium monoxide, potassium monoxide, potassium monoxide, magnesium oxide, barium oxide, strontium oxide, calcium oxide, beryllium oxide, cesium oxide, rubidium oxide and lithium oxide. The preferred basic agents are sodium or potassium carbonate or hydroxide, and most preferably ammonia, in the form of an aqueous solution.

To recap, types of useful basic agents are ammonia and the hydroxides, oxides alcoholates or carbonates of the alkaline or earth alkalime metals. The alkali metals are lithium, sodium, potassium, rubidium, cesium and francium. The alkaline earth metals are beryllium, magnesium, calcium, strontium, barium and radium.

The precipitated 2-amino-benzothiazole can be separated from the neutralized solution by any suitable means, and preferably by filtering off or centrifuging.

An advantage of the process of this invention is that is has a short reaction time and produces a pure product in a good yield.

To recap, the process of this invention includes adding phenylthiourea, in the absence of a solvent, to a cyclization agent and filtering the resultant salt of amino-benzothiazole from the reaction mixture.

Herein all parts, percentages, and ratios are expressed on a weight basis, unless otherwise stated or otherwise obvious herefrom to one ordinarily skilled in the art.

EXAMPLE 1

2-amino-6-methoxybenzothiazole 18.2 gm. (0.1 mole) of p-methoxyphenylthiourea were added to 100 ml of $S_2Cl_2$, while stirring. The reaction mixture was kept for 2 hrs. at 60° C. Subsequently the chlorohydrate formed was filtered and washed with $CH_2Cl_2$. After solution of the chlorohydrate in water and treatment with activated charcoal, the solution was neutralized with ammonia. The 2-amino-6-benzothiazole was filtered and dried in the vacuum.

The yield amounted to 16.4 gm. or 90.5 percent. The product had a purity of 99.3 percent and a melting point of 167° to 167.5° C.

EXAMPLE 2

2-amino-4-chlorobenzothiazole 18.6 gm. (0.1 mole) of o-chlorophenylthiourea was added to 100 ml of $S_2Cl_2$, while stirring. The reaction mixture was kept at 60° C. for 3 hrs. and then the chlorohydrate formed was filtered off and washed with $CH_2Cl_2$. The residue was absorbed in water, treated with activated charcoal and subsequently neutralized with ammonia. The precipitated 2-amino-4-chlorobenzothiazole was filtered and dried in the vacuum.

The yield amounted to 15 gm or 80 percent. The product had a purity of 98.5 percent and a melting point of 200° to 202°C.

What is claimed is:

1. A process for the production of a salt of a 2-amino-benzothiazole having the formula:

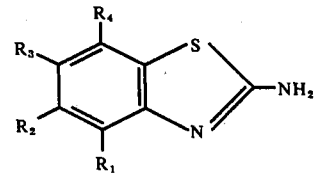

wherein $R_1$, $R_2$, $R_3$ and $R_4$ are the same or different and are hydrogen, halogen, alkyl having 1 to 10 carbon atoms or alkoxy having 1 to 10 carbon atoms, which comprises (a) adding a phenylthiourea having the formula:

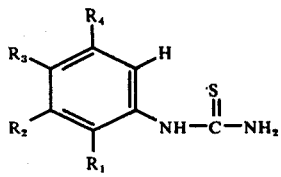

wherein $R_1$, $R_2$, $R_3$ and $R_4$ are defined as above, to a cyclization agent in the absence of a solvent and allowing said phenylthiourea to cyclize to form said 2-amino-benzothiazole in salt form, said cyclization step (a) being conducted for between 1 and 10 hours at a temperature between 30° and 100° C., said cyclization agent being a halogen, a sulfur halide, a sulfoxy halide, $SbI_5$, $SbF_5$ or $SbCl_5$, and said cyclization agent being present in an amount which is at least 6 times it stoichiometric amount, and (b) filtering said salt of said 2-amino-benzothiazole out of the reaction mixture of step (a).

2. A process as described in claim 1 wherein said cyclization of step (a) is conducted at a temperature between 50° and 60° C.

3. A process as described in claim 1 wherein said cyclization agent is a sulfur halide.

4. A process as described in claim 1 wherein said cyclization agent is disulfur dichloride.

5. A process as described in claim 1 wherein said cyclization agent is present in an amont which is between 10 and 12 times its stoichiometric amount.

6. A process as described in claim 1 wherein said salt of said 2-amino-benzothiazole, after step (b) is purified and placed in the free compound form.

7. A process as described in claim 1 wherein (i) said salt of said 2-amino-benzothiazole, after step (b) is washed with a solvent for said cyclization agent to remove any cyclization agent from said 2-amino-benzothiazole, (ii) said salt of said 2-amino-benzothiazole from step (i) is dissolved in water, (iii) the solution of step (ii) is neutralized with a basic agent, said 2-amino-benzothiazole precipitating in crystalline form, and (iv) removing said 2-aminobenzothiazole precipitate from said neutralized solution.

8. A process as described in claim 7, wherein, between steps (ii) and (iii) said solution (ii) is treated with activated charcoal to bleach and clarify said solution (ii) containing said salt of said 2-amino-benzothiazole.

9. A process as described in claim 7 wherein said basic agent is sodium or potassium carbonate or hydroxide in aqueous solution.

10. A process as described in claim 7 wherein said basic agent is an aqueous ammonia solution.

11. A process as described in claim 7 wherein said removal of step (iv) is achieved by filtration or centrifugation.

12. A process as described in claim 1 wherein $R_1$, $R_2$, $R_3$ and $R_4$ are the same or different and are alkyl having 1 to 4 carbon atoms.

13. A process as described in claim 1 wherein $R_1$, $R_2$, $R_3$ and $R_4$ are the same or different and are alkoxy having 1 to 4 carbon atoms.

14. A process as described in claim 1 wherein said cyclization agent is disulfur dichloride, bromine, chlorine, fluorine, iodine, sulfur monochloride, $S_2Br_2$, sulfur dichloride $SCl_2$, $SCl_4$, $S_2F_2$, $SF_4$, $S_2F_{10}$, $SF_6$, $SO_2Cl_2$, $S_2O_5Cl_2$, $SO_2F_2$, $SO_2ClF$, $SOBr_2$, $SOCl_2$, $SOF_2$, $SOClF$, $S_2OCl_4$, $S_2O_3Cl_4$, $SbI_5$, $SbF_5$ or $SbCl_5$.

* * * * *